US00PP26680P2

(12) United States Plant Patent
Lane et al.

(10) Patent No.: US PP26,680 P2
(45) Date of Patent: May 3, 2016

(54) ***PRUNUS* TREE NAMED 'SPC136'**

(50) Latin Name: *Prunus avium*
Varietal Denomination: SPC136

(71) Applicant: Her Majesty The Queen In Right Of Canada as Represented by the Minister of Agriculture and Agri-Food, Ottawa (CA)

(72) Inventors: William David Lane, Summerland (CA); Richard MacDonald, Summerland (CA)

(73) Assignee: Her Majesty the Queen in Right of Canada as Represented by the Minister of Agriculture and Agri-Food, Ottawa (CA)

( * ) Notice: Subject to any disclaimer, the term of this patent is extended or adjusted under 35 U.S.C. 154(b) by 133 days.

(21) Appl. No.: 13/999,433

(22) Filed: Feb. 25, 2014

Related U.S. Application Data

(60) Provisional application No. 61/852,379, filed on Mar. 15, 2013.

(51) Int. Cl.
*A01H 5/00* (2006.01)

(52) U.S. Cl.
USPC ..... Plt./181

(58) Field of Classification Search
USPC ..... Plt./181
See application file for complete search history.

(56) References Cited

PUBLICATIONS

PLUTO Plant Variety Database Jul. 22, 2015. p. 1.*

* cited by examiner

*Primary Examiner* — Annette Para
(74) *Attorney, Agent, or Firm* — Penny J. Aguirre

(57) ABSTRACT

A new cultivar of *Prunus avium*, 'SPC136', characterized by its mid-season fruit harvest, its flowers that are not self-fertile, lateness of bloom, its intermediate precocity of fruit bearing, its upright growth habit, its fruit skin that is wine red in color and flesh that is dark red to black in color, its large flowers with wide petals, and its firm, very large, kidney-shaped fruit.

1 Drawing Sheet

Botanical classification: *Prunus avium.*
Variety denomination: 'SPC136'.

BACKGROUND OF THE INVENTION

The present invention relates to a new and distinct cultivar of *Prunus avium* and will be referred to hereafter by its cultivar name, 'SPC136'. 'SPC136' is a new cultivar of sweet cherry tree grown for fruit production.

The new cultivar of *Prunus* arose from a breeding program conducted by the Inventor at a research centre in Summerland, B.C., Canada with the goal of developing a new cultivar of cherry tree that are firm and well-sized with good stem pull retention.

The new cultivar arose from a cross made in 1981 between a proprietary seedling from the Inventors breeding program, ref no. 2S-36-36 as the female parent and 'Summit' (not patented), as the male parent. The Inventor selected 'SPC136' as a single unique plant amongst the seedlings that resulted from the above cross in 1988.

Asexual propagation of the new cultivar was first accomplished by budding onto *Prunus avium* rootstock by the Inventor in Summerland, B.C., Canada in 1989. Asexual propagation by budding has determined that the characteristics of the new cultivar are stable and are reproduced true to type in successive generations.

SUMMARY OF THE INVENTION

The following traits have been repeatedly observed and represent the characteristics of the new cultivar as grown in test plots in Summerland, BC, Canada. These attributes in combination distinguish 'SPC136' as a unique cultivar of cherry tree.

1. 'SPC136' exhibits a mid-season fruit harvest.
2. 'SPC136' exhibits flowers that are not self-fertile.
3. 'SPC136' exhibits an intermediate precocity of fruit bearing.
4. 'SPC136' exhibits an upright growth habit.
5. 'SPC136' exhibits firm, very large, kidney-shaped fruit.
6. 'SPC136' exhibits fruit skin that is wine red in color and flesh that is dark red to black in color.
7. 'SPC136' exhibits large flowers with wide petals.

The male parent, 'Summit', is similar to 'SPC136' in bloom and harvest time and in being non self-fertile, but differs from 'SPC136' in having fruit that is less firm than 'SPC136'. The female parent, ref no. 2S-36-36, differs from 'SPC136' in having fruit that is much less firm. 'SPC136' can be most closely compared to the cultivars 'Van' (not patented), 'Sumnue' (not patented), and 'Santina' (not patented). 'Van' differs from 'SPC136' in having smaller flowers, shorter fruit stalks, fruit that is much smaller with a prominent suture, and in having a slightly later harvest season. 'Sumnue' differs from 'SPC136' in having smaller flowers, shorter fruit stalks, and fruit that is smaller. 'Santina' differs from 'SPC136' in having smaller flowers that are self-fertile, shorter fruit stalks, fruit that is smaller with a prominent suture, and in having a slightly earlier harvest season. 'Van', 'Sumnue', and 'Santina' all bloom earlier than 'SPC136'

BRIEF DESCRIPTION OF THE DRAWING

The accompanying color photograph illustrates the overall appearance and distinct characteristics of the fruit of 'SPC136' on an 8 year-old tree as grown in a trial plot in Summerland, B.C., Canada.

The photograph in FIG. 1 provides a view of a cluster of fruit of 'SPC136'. The colors in the photograph are as close as possible with the digital photography techniques available, the color values cited in the detailed botanical description accurately describe the colors of the cherry tree and fruit.

DETAILED BOTANICAL DESCRIPTION

The following is a detailed description of 8 year-old trees as grown in a trial plot in Summerland, B.C., Canada. The phenotype of the new cultivar may vary with variations in environmental, climatic, and cultural conditions, as it has not been tested under all possible environmental conditions. The color determination is in accordance with The 2001 R.H.S. Colour Chart of The Royal Horticultural Society, London, England, except where general color terms of ordinary dictionary significance are used.

General description:

*Plant type*.—Deciduous fruit bearing tree.

*Plant habit*.—Upright with medium crown density.

*Height and spread*.—Reaches about 3.0 m in height and about 2.5 m in width.

*Cold hardiness*.—U.S.D.A. Zone 4.

*Diseases and pests*.—No susceptibility or resistance to diseases or pests has been observed.

*Root description*.—Fibrous, freely branched.

*Propagation*.—Budding onto rootstock.

*Growth rate*.—Moderate.

Trunk description:

*Size of trunk*.—20.1 cm in diameter measured 38 cm above soil level.

*Bark color*.—202C with horizontal streaks of 187B.

*Bark texture*.—Rough and peeled.

Description of dormant shoots (one year-old):

*Pubescence*.—None.

*Shoot size*.—Average of 26 cm in length and 5.42 mm in width.

*Anthocyanin presence*.—None.

*Thickness of shoot at center of middle internode*.—Medium; average of 4.03 mm.

*Bark color*.—175A.

*Shoot angle*.—Erect.

*Lenticels*.—9.3 lenticels per 2 $cm^2$.

*Branch internode length*.—Short to medium; average of 42 mm.

*Vegetative buds*.—Large in size; 6.68 mm in length and 3.81 mm in width, conical to round in shape, adpressed to held slightly out from shoot, support is medium.

Description of growing shoots:

*Color of growing tip of shoot*.—175A.

*Pubescence of shoots tip*.—None.

*Anthocyanin presence*.—None.

Foliage description:

*Leaf shape*.—Broadly obovate to elliptical.

*Leaf division*.—Simple.

*Leaf base*.—Rounded.

*Leaf apex*.—Acute and acuminate at very tip.

*Leaf fragrance*.—None.

*Leaf burst*.—Early in the beginning of full flowering.

*Leaf venation*.—Pinnate, not prominent, same as leaf color with the midrib on lower surface.

*Leaf margins*.—Biserrate.

*Leaf arrangement*.—Alternate.

*Leaf aspect*.—Slightly concave and held horizontal to oblique downward in relation to shoot.

*Leaf attachment*.—Petiolate.

*Leaf surface*.—Glabrous and slightly glossy on upper surface and weakly to moderately pubescent on lower surface.

*Leaf size*.—Mature leaves average 15.8 cm in length and 8.3 cm in width.

*Leaf internodes*.—Average of 50 mm.

*Leaf color*.—Mature leaves upper surface; 139A, mature leaves lower surface; 138A, fall color occurs late in season.

*Petioles*.—Average of 2.5 cm in length and 2.46 mm in width, 178B in color with anthocyanin, 2 nectaries are round and 185B in color, glabrous surface.

Inflorescence description:

*Blooming period*.—Late bloom in BC, Canada.

*Inflorescence type*.—Clusters of single flowers.

*Lastingness of inflorescence*.—Average of 7-10 days.

*Flower buds*.—Ovoid, round tip in shape, about 5.75 mm in length and 3.57 mm in width prior to opening, 175A in color.

*Flower type*.—Rotate corolla above an elongated calyx with stamens and pistil extended.

*Flower size*.—Average of 3.7 cm in diameter.

*Calyx*.—Comprised of sepals fused into an ovoid base with un-fused portions spreading at apex.

*Sepals*.—5, 58A in color, glabrous surface, about 6.35 mm in length with un-fused portions, entire glandular margin, attenuate apex, fused base.

*Petals*.—5, broadly elliptic in shape, un-fused, thin and papery substance, smooth margin, oblique base, round apex, about 16.03 mm in length and 14.39 mm in width, 155D in color (upper and lower surface).

*Pedicels*.—Average of 36.14 nun in length, 1.39 mm in width, 144C in color, glabrous surface.

*Rachis*.—Glabrous surface, flowers lightly compacted with whorled arrangement.

Reproductive organs:

*Gynoecium*.—1 pistil about 12.4 mm in length and 1 mm in width extending beyond perianth, style is 25C in color, stigma is about 1 mm in diameter, ovary is superior, glabrous and 143C in color.

*Androcoecium*.—Average of 25 stamens, base adnate to calyx, filaments are 155A in color, about 12.4 mm in length and 1 mm in width, anthers are 162A in color, dorsifixed, about 0.5 mm in length and in width, pollen is abundant in quantity and about 162A in color.

*Fertility*.—Not self-fertile. S alleles are S2 and S4.

Fruit description:

*Fruit type*.—Drupe.

*Fruit shape*.—Kidney to cordate.

*Fruit apex*.—Flat with moderate susceptibility to rain induced cracking.

*Fruit size*.—Large, 30.5 mm in length and 26.15 mm in width.

*Fruit firmness*.—Firm.

*Fruit set*.—Medium.

*Fruit stalk*.—Long and medium in thickness; 4.6 cm in length and 1.45 mm in width, color 144A.

*Fruit bearing*.—Intermediate precocity.
*Skin color*.—Deep dark black purple red when ripe with a light colored dots.
*Harvest date*.—Very early to early; July 9 in Summerland, BC, Canada.
*Skin surface*.—Glossy.
*Skin suture*.—Low prominence.
*Flesh color*.—Red.
*Juice*.—Strong juiciness and red in color.
*Flesh texture*.—Fleshy, moderately juicy.
*Flavor*.—Medium sweetness.
*Weight*.—12.9 g/drupe.
*Brix*.—20.
*Acidity*.—Low pH 3.74.
*Seeds*.—1 stone per drupe, large in size; average of 12.09 mm in length and 9.89 mm in width and medium in comparison to fruit, shape; lateral view is symmetrical, non adherent to flesh, front view is obovate, basal view is round, keel is strongly developed.

It is claimed:

1. A new and distinct cultivar of *Prunus* tree named 'SPC136' as herein illustrated and described.

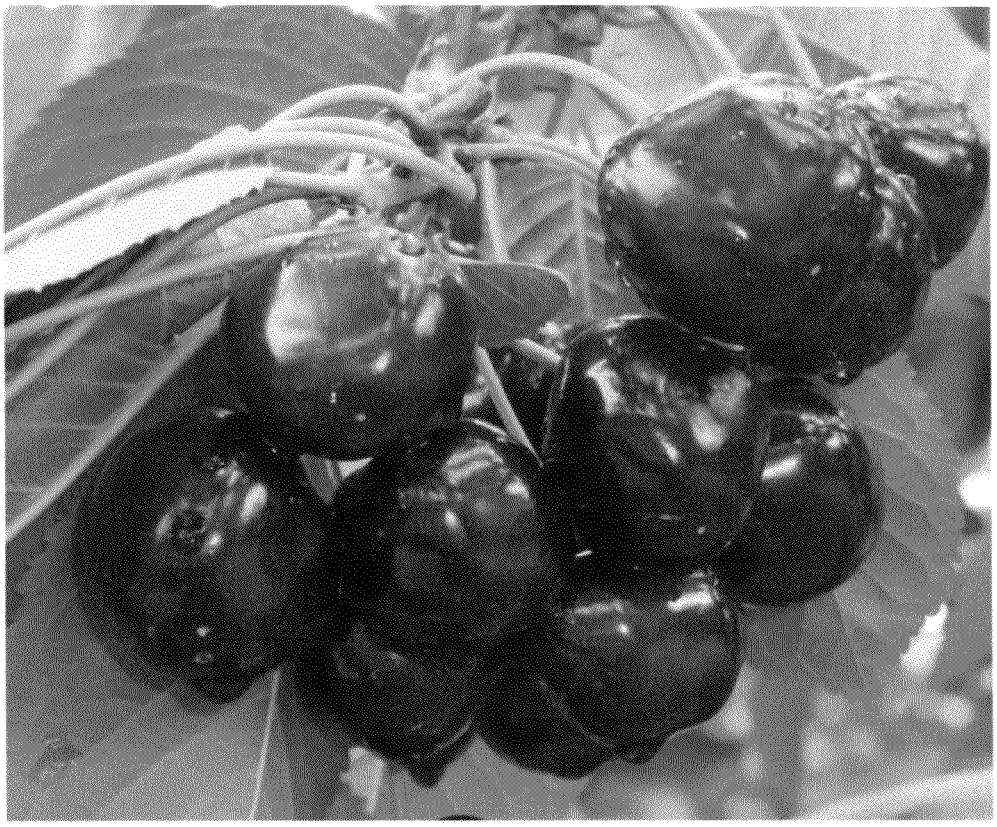

* * * * *